(12) United States Patent
Park (10) Patent No.: US 7,963,918 B2
(45) Date of Patent: Jun. 21, 2011

(54) APPARATUS FOR ULTRASONIC EXAMINATION OF DEFORMABLE OBJECT

(76) Inventor: Hee-Boong Park, Sungnam-si (KR)

( * ) Notice: Subject to any disclaimer, the term of this patent is extended or adjusted under 35 U.S.C. 154(b) by 50 days.

(21) Appl. No.: 10/540,319

(22) PCT Filed: Jan. 17, 2004

(86) PCT No.: PCT/KR2004/000077
§ 371 (c)(1), (2), (4) Date: Jun. 21, 2005

(87) PCT Pub. No.: WO2004/064644
PCT Pub. Date: Aug. 5, 2004

(65) Prior Publication Data
US 2006/0084868 A1    Apr. 20, 2006

(30) Foreign Application Priority Data

Jan. 17, 2003   (KR) .................. 10-2003-0003218

(51) Int. Cl.
*A61B 8/00* (2006.01)
(52) U.S. Cl. ........ 600/437; 600/407; 600/427; 600/440; 378/21; 378/37
(58) Field of Classification Search .................. 600/427, 600/429, 461, 437, 440, 130, 169, 407; 382/132, 382/284; 378/21, 37
See application file for complete search history.

(56) References Cited

U.S. PATENT DOCUMENTS

| | | | | |
|---|---|---|---|---|
| 3,556,081 A | * | 1/1971 | Jones | 600/437 |
| 3,585,847 A | * | 6/1971 | Brenden | 73/605 |
| 4,211,949 A | * | 7/1980 | Brisken et al. | 310/322 |
| 4,233,988 A | * | 11/1980 | Dick et al. | 600/445 |
| 4,248,090 A | * | 2/1981 | Glenn | 73/620 |
| 4,274,421 A | * | 6/1981 | Dory | 600/446 |
| 5,603,326 A | * | 2/1997 | Richter | 600/443 |
| 5,664,573 A | * | 9/1997 | Shmulewitz | 600/445 |

(Continued)

FOREIGN PATENT DOCUMENTS

DE    199 02 521 A1    7/2000

(Continued)

*Primary Examiner* — Brian Casler
*Assistant Examiner* — Joel M Lamprecht
(74) *Attorney, Agent, or Firm* — Knobbe Martens Olson & Bear LLP (57) ABSTRACT

The present invention relates to an apparatus for an ultrasonic examination of a deformable object, particularly, the breast. More particularly, the present invention relates to an apparatus capable of performing an ultrasonic examination by moving an ultrasonic probe while maintaining the position and shape of a deformable object to be inspected. That is, the present invention relates to an apparatus capable of performing an effective ultrasonic by scanning an entire deformable object such as the breast at one time using a movable ultrasonic probe. The apparatus of the present invention comprises a supporting frame; a movable means which has a flat surface with rigidity widthwise on which the deformable object is placed and is installed in the frame to move forward and rearward at a certain moving distance in a longitudinal direction of the frame; a driving means for moving the movable means forward and rearward; and at least one ultrasonic probe disposed to extend widthwise of the movable means, a ultrasonic wave transmission/reception surface of the ultrasonic probe being substantially flush with an upper surface of the movable means, the ultrasonic probe being fixed to the movable means at a position inward form longitudinal both ends of the movable means by a distance smaller than the moving distance of the movable means.

14 Claims, 8 Drawing Sheets

U.S. PATENT DOCUMENTS

| | | | | |
|---|---|---|---|---|
| 5,776,062 | A | * 7/1998 | Nields | 600/407 |
| 5,820,552 | A | * 10/1998 | Crosby et al. | 600/407 |
| 5,833,627 | A | * 11/1998 | Shmulewitz et al. | 600/562 |
| 5,840,022 | A | * 11/1998 | Richter | 600/407 |
| 5,938,613 | A | * 8/1999 | Shmulewitz | 600/461 |
| 5,983,123 | A | * 11/1999 | Shmulewitz | 600/407 |
| 6,027,457 | A | * 2/2000 | Shmulewitz et al. | 600/562 |
| 6,102,866 | A | * 8/2000 | Nields et al. | 600/461 |
| 6,214,018 | B1 | * 4/2001 | Kreizman et al. | 606/130 |
| 6,459,925 | B1 | * 10/2002 | Nields et al. | 600/427 |
| 7,103,205 | B2 | * 9/2006 | Wang et al. | 382/132 |
| 2006/0241423 | A1 | * 10/2006 | Anderson et al. | 600/437 |

FOREIGN PATENT DOCUMENTS

| | | |
|---|---|---|
| JP | 4183452 | 6/1992 |
| JP | 11192231 | 7/1999 |
| JP | 2002336256 | 11/2002 |
| WO | WO 83/02053 | 6/1983 |

* cited by examiner

APPARATUS FOR ULTRASONIC EXAMINATION OF DEFORMABLE OBJECT

TECHNICAL FIELD

The present invention relates to an apparatus for an ultrasonic examination of a deformable object, particularly, the breast. More particularly, the present invention relates to an apparatus capable of performing an ultrasonic examination by moving an ultrasonic probe while maintaining the position and shape of a deformable object to be inspected. That is, the present invention relates to an apparatus capable of performing an effective ultrasonic examination by scanning an entire deformable object such as the breast at one time using a movable ultrasonic probe.

BACKGROUND ART

Generally, breast cancer is the most common carcinoma in the Western countries, and also has a high frequency of occurrence together with cervical cancer and stomach cancer for Korean women. To diagnose breast cancer, mammography is generally used as a primary diagnosis. The mammography has been widely used since it has an advantage in that a diagnosis can be very simply made. However, if the tissue of the breast is very dense, diagnostic sensitivity and specificity are considerably lowered. Especially, in case of Korean women, since the tissue of the breast is denser than that of Western women, the effectiveness of the mammography is greatly lowered and diagnosis of breast cancer is very difficult.

Recently, instead of the mammography, an ultrasonic examination has been introduced and used. The ultrasonic examination does not involve a risk of radiation, and can diagnose a small tumor having a size of 2 to 3 mm due to significant improvement of image processing technology. Conventional ultrasonic examination methods include an examination method in which an inspector holds an ultrasonic probe of about 5 centimeters and moves it on a desired region of a standing subject to be examined. However, the method requires much time and manpower for carrying out the examination, and is very inefficient for mass screening examination. Further, such an examination process gives physical fatigue to an inspector and causes a subject to feel discomfort and shame. Furthermore, since the inspector moves the ultrasonic probe with his/her hand to perform the examination, only the inspector can know information on an examined location of an object to be examined. Thus, this may cause incorrect recordation of examination results. In addition, there are problems in that the examination process depends mostly on subjective evaluation by the inspector and reliability may be lowered unless the inspector has much skill in the examination. Moreover, the ultrasonic probe should be completely in close contact with the object to be examined to correctly perform the examination. However, when the examination is carried out, the ultrasonic probe and the object to be examined are not completely in close contact with each other so that a gap is formed therebetween and the results of diagnosis becomes very incorrect. In particular, in a case where the subject maintains a standing posture during the examination, since an upper side of the breast is pressed while a lower side thereof is supported, the subject feels a pain so that the subject may tend to avoid the examination. Further, in a case where the subject lies on his/her back or stomach during the ultrasonic examination, since the examination procedure is very complicated, the efficiency of the examination apparatus is lowered. Moreover, since the subject goes through an examination in an uncomfortable posture, the subject feels physical fatigue.

International Patent Application Publication No. WO 83/02053 discloses an apparatus capable of performing an ultrasonic examination of a deformable object, wherein the breast is placed on an ultrasonically transparent plate through which ultrasonic waves can pass and an ultrasonic sensor is moved below the plate. An object of the patent application is to provide an examination apparatus that can perform an ultrasonic examination in a posture in which the results of an X-ray examination and the results of an ultrasonic examination can be more correctly compared with each other. In the examination apparatus disclosed in the patent application, however, since the plate through which the ultrasonic waves pass has not sufficient rigidity, deformation occurs when the breast is placed on the plate. Therefore, there is a drawback in that correct location information on the examination results cannot be obtained. If the thickness of the plate through which the ultrasonic waves pass is increased in order to prevent deformation, there are drawbacks in that an image is not clear and examination results are incorrect.

DISCLOSURE OF INVENTION

The present invention is conceived to solve the aforementioned problems. An object of the present invention is to provide an apparatus for an ultrasonic examination, wherein a subject can simply go through an examination in a standing posture and a location of a deformable object such as the breast corresponding to ultrasonic examination results can be accurately obtained.

Another object of the present invention is to provide an apparatus for an ultrasonic examination, wherein an object to be examined can be automatically scanned from a lower portion thereof without holding an ultrasonic probe with a hand by an inspector and the ultrasonic probe can come into contact with the object to be examined by means of gravity without pressing the object to be examined, in particular, to provide an apparatus for an ultrasonic examination, wherein when a gel pad is used, an ultrasonic examination can be performed in a state where the ultrasonic probe is completely in close contact with the object to be examined while the object to be examined presses the gel pad.

A further object of the present invention is to provide an apparatus for an ultrasonic examination, wherein an ultrasonic examination can be quickly performed by moving an ultrasonic probe in a state where the location and shape of a deformable object to be examined are maintained, thereby examination with this apparatus can be efficiently performed in case of mass screening of breast cancer.

A still further object of the present invention is to provide an apparatus for an ultrasonic examination, wherein the height and orientation of the apparatus can be freely adjusted according to a physical figure of a subject and a region thereof to be examined.

According to the present invention for achieving the objects, there is provided an apparatus for an ultrasonic examination, comprising a supporting frame; a movable means which has a flat surface with rigidity widthwise on which the deformable object is placed and is installed in the frame to move forward and rearward at a certain moving distance in a longitudinal direction of the frame; a driving means for moving the movable means forward and rearward; and at least one ultrasonic probe disposed to extend widthwise of the movable means, a ultrasonic wave transmission/reception surface of the ultrasonic probe being substantially flush with an upper surface of the movable means, the ultrasonic probe being fixed to the movable means at a position inward from longitudinal both ends of the movable means by a distance smaller than the moving distance of the movable means.

In the apparatus of the present invention, the movable means may comprise a caterpillar consisting of a plurality of links each of which has a flat surface, a pair of rollers for internally supporting both longitudinal ends of the caterpillar, and a pair of supporting members for supporting both lateral sides of the caterpillar. At least one of the pair of the rollers may be interlocked with the caterpillar to move the caterpillar in response to the rotation of the roller. The driving means may be coupled to and rotates the interlocked roller. The at least one ultrasonic probe may be fixedly installed between two links of the caterpillar.

Further, in the apparatus of the present invention, the movable means may comprise a caterpillar consisting of a plurality of links each of which has a flat surface, a pair of rollers for internally supporting both longitudinal ends of the caterpillar, and a pair of supporting members for supporting both lateral sides of the caterpillar, the driving means may be coupled to and rotates the caterpillar, and the at least one ultrasonic probe may be fixedly installed between two links of the caterpillar.

Furthermore, in the apparatus of the present invention, the ultrasonic probe is preferably a phased array scanning type probe capable of examining a large area.

Moreover, it is preferred that the apparatus of the present invention further comprise a height adjusting means for supporting the frame in such a manner that the height of the frame can be adjusted, thereby freely adjusting the height and orientation of the apparatus. The apparatus may further comprise a height adjusting means for supporting the frame in such a manner that the height of the frame can be adjusted; and a pressing means fixed to the height adjusting means to press the deformable object placed on the flat surface of the movable means. The apparatus of the present invention may further comprise a stand for supporting the height adjusting means; and a rotational shaft having one end supported rotatably by the stand and the other end fixed to a side surface of the height adjusting means, which is opposite to a side surface of the height adjusting means with the frame installed thereon.

Moreover, for a case where the tissue of an affected part is sampled to perform a histologic examination according to examination results, it is preferred that the ultrasonic examination apparatus of the invention further comprise a pressing means fixed to the height adjusting means to press the deformable object placed on the flat surface of the movable means.

The apparatus for the ultrasonic examination of the breast according to the present invention may comprise a height-adjustable stand; a height adjusting means connected rotatably to the stand and extending vertically; a scanning unit that is provided at a side of a lower portion of the height adjusting means and has an ultrasonic probe; a gel pad placed on the scanning unit; and a pressing means installed to move vertically above the gel pad.

The scanning unit comprises a hollow frame with an open upper face; a pair of rollers installed at both side ends of an inner space of the frame; a movable means that is installed around the pair of rollers in the form of a crawler to move in endless track manner and has an upper outer surface substantially flush with the upper face of the frame; a driving means for moving the movable means in endless track manner within a certain range; and an ultrasonic probe that is linearly and fixedly arranged to the movable means to move in the frame along the movable means and has an upper outer surface substantially flush with the upper outer surface of the movable means. The driving means comprises a motor having a rotational shaft connected to at least one of the pair of rollers, and a control unit for controlling the motor.

Further, the scanning unit may comprise a hollow frame having both open side faces; a movable means received in the frame to extrude through the both open side faces and to reciprocate toward the side faces of the frame; a driving means for reciprocating the movable means; and an ultrasonic probe that is linearly arranged within the movable means so as to have an upper surface substantially flush with an upper surface of the movable means and reciprocates together with the movable means within the frame.

Moreover, it is preferred that the length of the ultrasonic probe is 15 to 20 cm suitable for an examination of the breast.

Furthermore, it is preferred that the stand consist of upper and lower stands, and the upper stand be inserted into the lower stand to move vertically.

In addition, it is preferred that the gel pad be in a semi-solid gel state so that the gel pad maintains a certain shape to reduce friction between an object to be examined and the ultrasonic probe and the movable means. It is more preferred that the gel pad be constructed by filling a gel into an enclosure made of a sonolucent solid or flexible material.

EXPLANATION OF REFERENCE NUMERALS
FOR DESIGNATING MAIN COMPONENTS IN
THE DRAWINGS

10: Lower stand
12: Upper stand
20: Height adjusting means
22: Rotational shaft
40, 140: Ultrasonic scanning unit
42, 142: Frame
44, 144: Flat surface
46, 146: Ultrasonic probe
47: Roller
50: Gel pad
60: Pressing means
62: Guide groove
80: Driving means

BEST MODE FOR CARRYING OUT THE INVENTION

Hereinafter, preferred embodiments of the present invention will be described in detail with reference to accompanying drawings. The terms or words used herein should not be construed as being confined to common meanings or dictionary meanings but be construed as meanings and concepts matching with the technical spirit of the present invention based on the principle that an inventor can properly define the concept of a term to describe his/her invention in the best fashion. Therefore, the constitutions described herein and illustrated in the drawings do not cover all the technical spirit of the present invention but are merely the most preferred embodiments of the present invention. Thus, it should be understood that various equivalents and modifications can be made to the embodiments at the time of filing this application.

Figure 1:
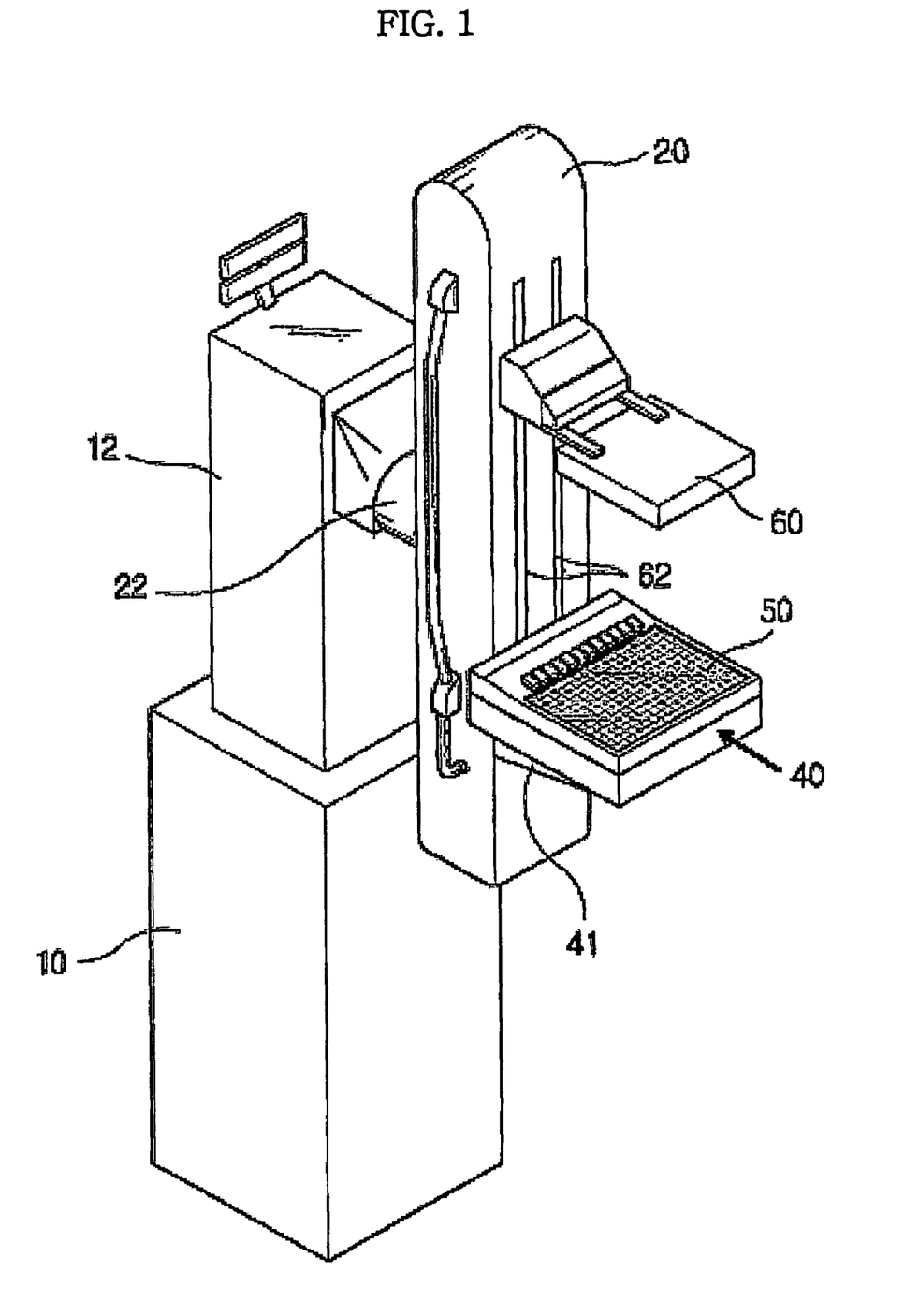
FIG. 1 is a perspective view showing an apparatus for an ultrasonic examination of the breast according to an embodiment of the present invention.

FIG. 1 is a view showing the entire configuration of an apparatus for an ultrasonic examination of the breast according to an embodiment of the present invention. Referring to FIG. 1, the apparatus for the ultrasonic examination of the breast (hereinafter, referred to as "ultrasonic examination apparatus") according to the embodiment of the present invention is provided with a stand mounted on an installation surface of an examination site.

The stand consists of a lower stand 10 and an upper stand 12. A portion of the upper stand 12 is inserted into the lower stand 10 to move vertically. That is, the height of a height adjusting means 20 to be described later is adjusted by the vertical movement of the upper stand 12. The vertical movement of the upper stand 12 can be accomplished by a mechanical means or electric-powered means without being limited to a specific means. Further, a plurality of wheels not shown may be provided at a lower end of the lower stand 10 to facilitate movement of the ultrasonic examination apparatus.

The height adjusting means 20 is coupled to the stands 10 and 12, particularly the upper stand 12. The height adjusting means 20 is a unit on which a variety of devices for an ultrasonic diagnosis and is elongated vertically. At this time, the height adjusting means 20 is fixed to one end of a rotational shaft 22 of which the other end is rotatably supported by the upper stand 12. That is, since the height adjusting means 20 is elongated vertically, an inclination of the height adjusting means 20 varies when the height adjusting means is rotated by the rotational shaft 22. The rotation of the height adjusting means 20 can be performed in a mechanical or electric-powered manner. Preferably, the height adjusting means may be remotely controlled by an additional operation means not shown for operating the ultrasonic examination apparatus.

A scanning unit 40 is provided at a side of the height adjusting means 20, which is opposite to the side thereof to which the rotational shaft 22 is coupled. The scanning unit 40 is to obtain an ultrasonic image for an object to be examined. The detailed structure thereof will be described later. The scanning unit 40 is installed at a portion of a lower end of the height adjusting means 20. Preferably, the scanning unit 40 is stably fixed on a supporting frame 41 formed integrally with the height adjusting means 20.

When an examination is performed, a gel pad 50 is disposed on the scanning unit 40. It is preferred that the gel pad 50 be in a semi-solid gel state so that the gel pad maintains a certain shape to reduce friction between the object to be examined and the ultrasonic probe and a movable means. It is more preferred that the gel pad be constructed by filling a gel into an enclosure made of a sonolucent solid or flexible material. Moreover, the gel pad 50 is in contact with the scanning unit 40, preferably, the movable means within the scanning unit 40 and an upper surface of the ultrasonic probe. In addition, the gel pad 50 made of a flexible material may be fixed to an upper surface of the scanning unit 40 by means of an additional frame such that the location of the gel pad cannot vary. When the ultrasonic probe 46 scans the object to be examined, a space formed between the object to be examined and the ultrasonic probe 46 is completely filled with the gel pad 50 so that a superior ultrasonic image can be obtained. In particular, since the enclosure of the gel pad 50 is made of a flexible material, the object to be examined presses the gel pad 50. Therefore, the space between the object to be examined and the ultrasonic probe 46 can be completely eliminated. Of course, the gel pad 50 is made of a known material through which ultrasonic waves can be transmitted without any loss.

A pressing unit 60 is installed at a position spaced apart by a certain distance upward from the gel pad 50. The pressing unit 60 can be moved vertically along guide grooves 62 formed on an outer surface of the height adjusting means 20. Although not shown, a driving means for vertically moving the pressing unit 60 is installed within the height adjusting means 20. Of course, although the pressing unit 60 can be moved vertically in a mechanical manner, it is preferred that the pressing unit 60 be remotely controlled by an external operation means so that the vertical movement can be performed in an electric-powered manner.

Figure 2:
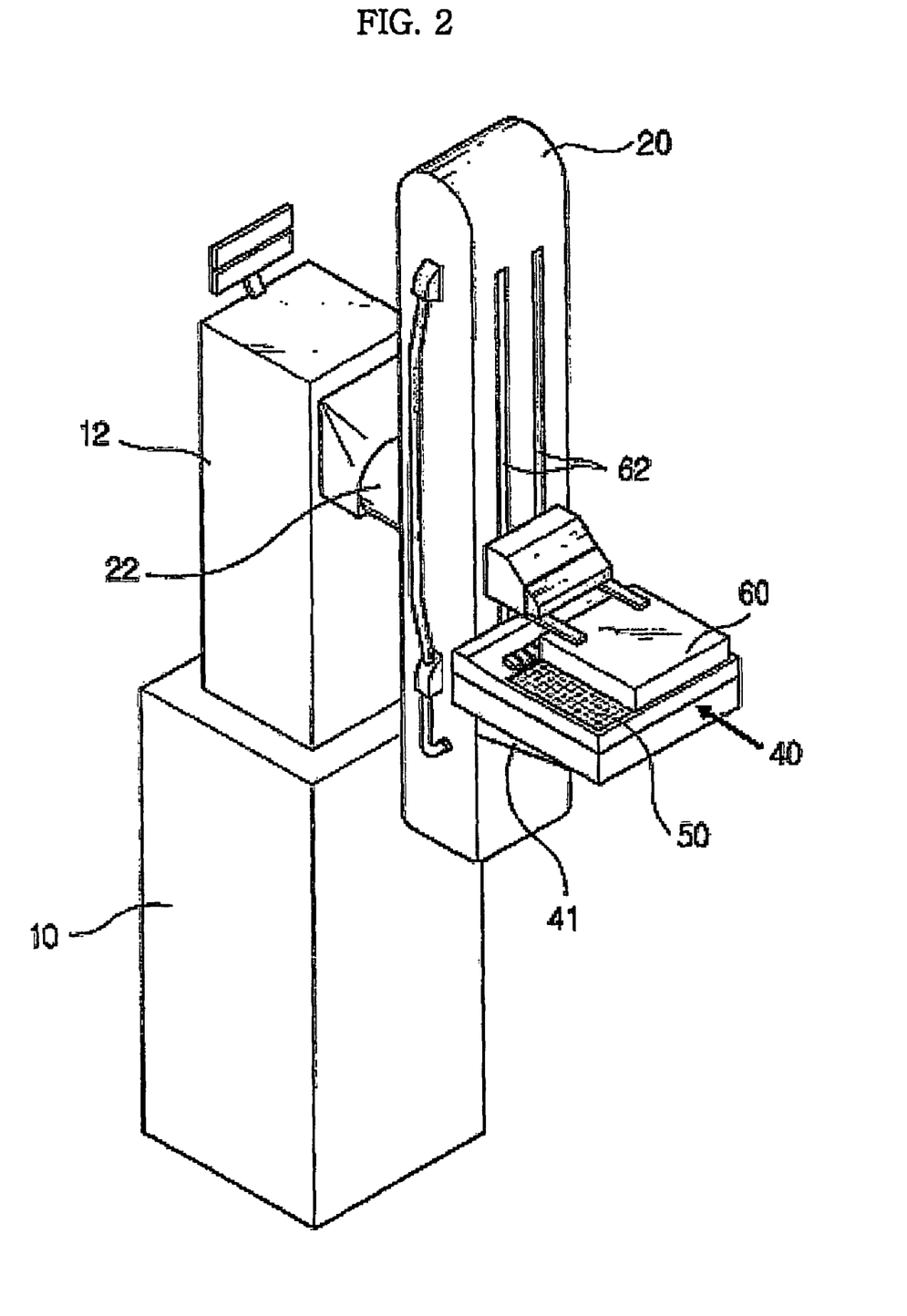
FIG. 2 is a perspective view showing a state where a pressing unit of the ultrasonic examination apparatus of FIG. 1 has been moved downward.

In a state where the object to be examiner is placed on the gel pad 50, the pressing unit 60 is moved downward to press the object to be examiner. At this time, a state where the pressing unit 60 has been moved downward is shown in FIG. 2.

Figure 3:
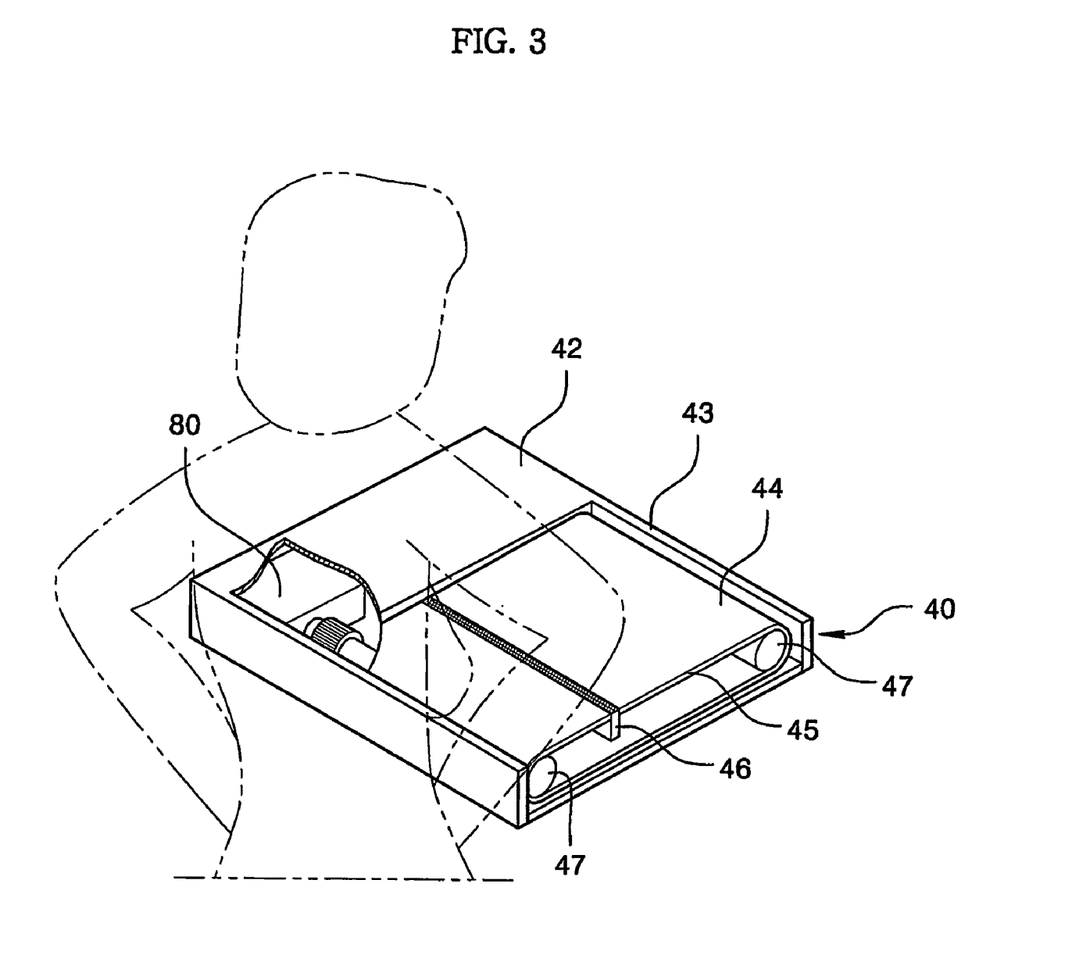
FIG. 3 is a perspective view showing a first embodiment of a scanning unit of the ultrasonic examination apparatus according to the present invention.

FIG. 3 shows a first embodiment of the scanning unit 40 used in the ultrasonic examination apparatus according to the embodiment of the present invention. In this embodiment, the scanning unit 40 comprises a hollow frame 42 having an at least partially open upper face and a generally rectangular space formed therein. The movable means is installed within the inner space of the frame 42. The movable means comprises a pair of rollers 47 installed at both sides 43 of the inner space of the frame 42 and a belt 45 installed movably while surrounding the rollers. The belt 45 has a flat upper surface 44 on which the breast as the object to be examined is placed. At least one of the pair of rollers 47 is coupled to a separate driving means 80 to move the belt 45 in endless track manner. The driving means 80 comprises a motor coupled to the roller 47 and a control unit for controlling the motor. Since a technique for controlling the position of the belt by controlling the motor is obvious to those skilled in the art, a description thereof will be omitted. Preferably, the other roller which is not coupled to the motor is a driven roller or idle roller and serves to stably guide the belt 45 when the belt 45 is moved in endless track manner.

The ultrasonic probe 46 is provided at the belt 45. The ultrasonic probe 46 is fixedly coupled to the belt 45 such that a transmission/reception surface of the ultrasonic probe 46 is substantially flush with the flat surface 44 of the belt 45 to move together with the belt 45. Preferably, the ultrasonic probe 46 is linearly arranged widthwise of the belt 45, i.e. in a direction perpendicular to the movement direction of the belt 45.

That is, it is preferred that the ultrasonic probe 46 have an upper surface flush with the flat surface 44. Therefore, the flat surface 44 and the upper surface of the ultrasonic probe 46 define a single plane within the inner space of the frame 42. Preferably, the belt 45 is pulled under proper tension to maintain flatness thereof against vertical pressure, and has flexibility in the movement direction and sufficient rigidity widthwise. In order to prevent the belt 45 from being deformed widthwise and to guide the movement thereof, although not shown, a support member may be installed within a space formed between upper and lower portions of the belt 45 constituting an endless track.

Preferably, the flat surface 44 and the upper surface of the ultrasonic probe 46 define the same plane as defined by the adjacent sides of the frame 42 or the entire frame 42. With such a structure, even though the gel pad 50 placed on the flat surface 44 and the ultrasonic probe 46 is made of a flexible material, the gel pad 50 can be supported stably. Further, even when the object to be examined is pressed by the pressing unit 60, the movable means dose not cause movement or deformation of the object to be examined and also hardly cause friction between the gel pad 50 and the ultrasonic probe 46.

At this time, it is preferred that the linearly arranged ultrasonic probe 46 have a length of about 15 to 20 cm as a whole and a relatively very narrow width. The overall length of the ultrasonic probe 46 should be sufficient to cover the entire object to be examined. Thus, the aforementioned length is determined from such a viewpoint.

The ultrasonic probe 46 is an expensive part that emits an ultrasonic wave to the object to be examined and then receives the reflected ultrasonic wave to obtain an image signal for the object to be examined. Therefore, in order to reduce costs, instead of a single probe having a length of 15 to 20 cm, a plurality of short probes may be connected to one another in end-to-end manner or in a state where some portions of adjacent probes overlap with each other at their sides, and image processing is performed to cover the entire width defined by the probes. At this time, an important feature of the ultrasonic probe 46 of the present invention is that the ultrasonic probe 46 is moved by the belt 45 through the entire width of the object to be examined so as to examine the entire object with single scanning. Although not shown, it is apparent that an additional ultrasonic wave generator is installed to provide the ultrasonic wave through the ultrasonic probe 46. Further, an additional Doppler device for analyzing the reflected ultrasonic wave is connected to the ultrasonic probe 46. As for the ultrasonic probe, it is desirable to use a phased array scanning type probe capable of inspecting a large range.

The driving means 80 comprising the motor serves to issue a command to various components or obtain necessary information and transmit the information to the components according to a processing routine installed in the driving means itself or a command of an external operating means. For example, when a control unit of the driving means 80 determines that the object to be examined is sufficiently pressed by the pressing unit 60 or receives a command from the external operating means in a state where the object to be examined is placed on the gel pad 50, the control unit issues a driving command to the motor and simultaneously instructs the ultrasonic probe 46 to emit the ultrasonic wave. Further, the control unit creates an image by using the ultrasonic wave emitted by the ultrasonic probe 46 and reflected from the object to be examined and stores the created image or transmit the image to an external display device.

Although not shown, an additional position sensor is attached to the belt 45 or the ultrasonic probe 46 of the scanning unit 40 to continuously sense the current position of the ultrasonic probe 46. The position sensor continuously informs a location at which the ultrasonic probe 46 currently performs an examination, so that the location can be caused to correspond to a relevant image. This location can be very usefully utilized later when the apparatus performs a diagnosis of a person to be examined. That is, when the image is analyzed to diagnose a person to be examined, the location information obtained from the position sensor can correctly inform the location of a region of the object to be examined at which a problem occurs.

Although the control unit has been illustrated as being installed within the scanning unit 40, the installation position of the control unit is not necessarily limited thereto. For example, the control unit may be provided within the height adjusting means 20 or may be installed separately outside of the apparatus together with a monitor and the like to construct a kind of computer that provides general functions such as user operation, image display and the like.

The ultrasonic examination apparatus according to the present invention constructed as above operates as follows.

First, to diagnose a subject, an inspector adjusts the height and inclination of the height adjusting means 20 to be fit for a physical figure of the subject. The height of the height adjusting means 20 is adjusted by operating the upper stand 12 upward or downward, and the inclination thereof is adjusted by rotating the rotational shaft 22. Next, in a state where the height and inclination of the height adjusting means have been adjusted, the subject puts his/her object to be examined on the gel pad 50, and the pressing unit 60 is then moved downward to press the object to be examined. The object to be examined that has been pressed by the pressing unit 60 is completely in close contact with the gel pad 50.

When the object to be examined has been completely pressed, the control unit operates an ultrasonic wave generator (not shown) to emit an ultrasonic wave through the ultrasonic probe 46. At the same time, the control unit operates the motor to rotate the roller 47. Thus, the belt 45 is slowly moved by the roller 47 in endless track manner. The movable means 44 is moved in endless track manner until the ultrasonic probe 46 is fully moved from one side to the other side of the object to be examined. During the movement of the movable means 44, the ultrasonic probe 46 ultrasonically scans the entire object to be examined at one time. During the scanning of the object to be examiner, the ultrasonic wave reflected from the object is analyzed by a Doppler device (not shown) and the analysis results are transmitted to the control unit. The analysis results are converted into an image that in turn is stored and simultaneously output to the outside through an additional display device. Further, during the movement of the belt 45, the position sensor (not shown) installed on the belt 45 or the ultrasonic probe 46 continuously detects the current location of the ultrasonic probe 46, and transmits the detected location to the control unit to match it with an image corresponding thereto. Accordingly, the image acquired from the object to be examined is stored while it is matched with the relevant location of the ultrasonic probe 46, and a three-dimensional image can be obtained by using the acquired image.

When the examination process has been completed, the control unit stops the operations of the motor and the ultrasonic wave generator.

Meanwhile, when another part of the breast of the subject is intended to be examined, the above process can be repeated in a state where the other object to be examined is placed on the gel pad 50. Further, when a side of the object is intended to be examined, the examination can be performed by rotating the height adjusting means 20 through the rotational shaft 22.

Although the process of examining an object to be examined by pressing the object by the pressing unit 60 has been described in this embodiment, it is possible to perform the examination under the control of the control unit in a state where the object to be examined is not pressed by the pressing unit.

Figure 4:
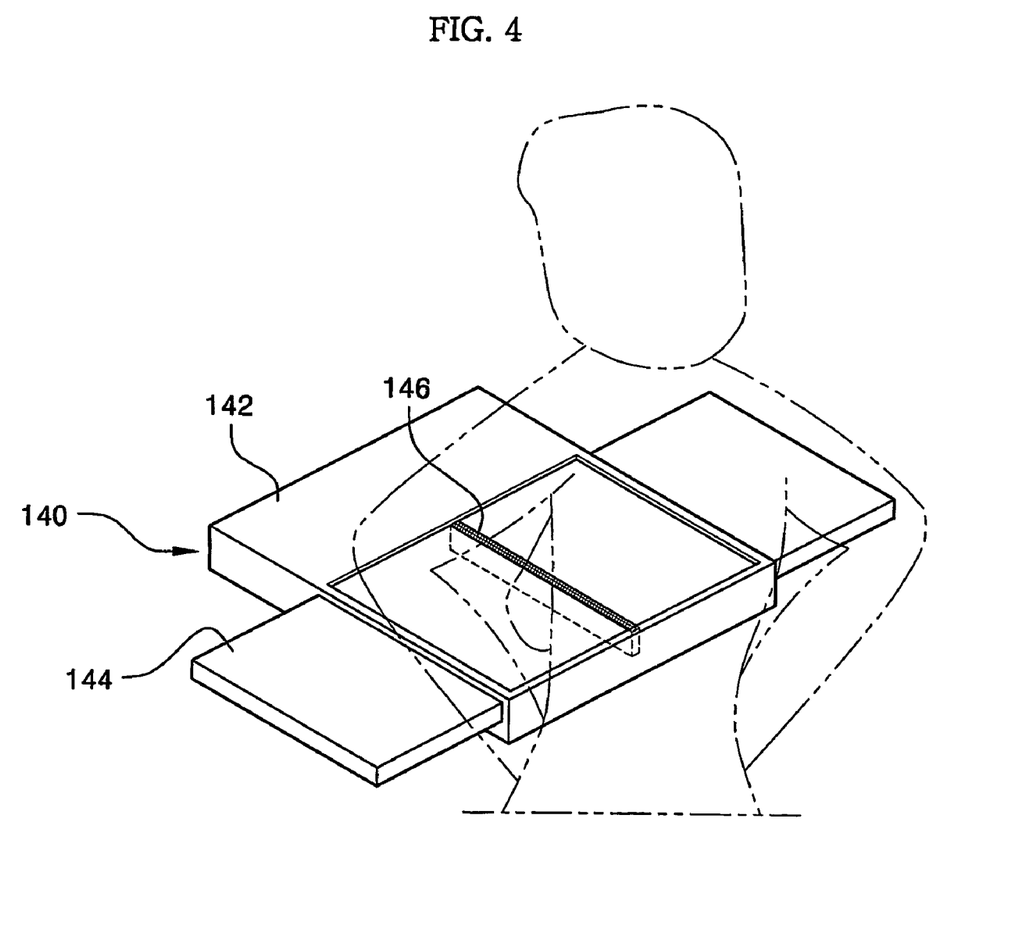
FIG. 4 is a perspective view showing a second embodiment of the scanning unit of the ultrasonic examination apparatus according to the present invention.

FIG. 4 shows a second embodiment of the scanning unit used in the ultrasonic examination apparatus of the present invention. Although the movable means 40 has been constructed using a belt moving in endless track manner in the embodiment of FIG. 3, a movable means 140 of this embodiment is constructed to move slidably.

That is, referring to FIG. 4, a frame 142 of the scanning unit 140 has partially open both side faces and an open upper face. Further, the frame 142 has a hollow configuration in which a space is formed therein. At this time, a movable means 144 generally taking the shape of a hexahedron is installed within the frame 142, and has a length that is approximately twice as large as the width of the frame 142 so that the movable means 144 can be installed to protrude through the both open side faces 143 of the frame 142. In this state, the movable means 144 can be moved slidably toward the both side faces of the frame 142.

Further, an ultrasonic probe 146 similar to that of the embodiment shown in FIG. 3 is linearly arranged within the movable means 144. A transmission/reception surface of the ultrasonic probe 146 is flush with a flat surface of the movable means 144 to define the same upper surface. Accordingly, the movable means 144 and the ultrasonic probe 146 can stably support the gel pad 50 made of a flexible material.

In this embodiment, a method of moving the movable means 144 can be implemented in various manners such as a manner in which lower rollers are installed to achieve the movement, and a manner in which a rack and a pinion are used to achieve the movement. However, the method is not limited to the specific examples. Although the scanning unit 140 of this embodiment constructed as above differs from the scanning unit shown in FIG. 3 in view of their overall structures and methods of moving the movable means, the scanning unit 140 operates based on the same principle as the scanning unit of FIG. 3. Therefore, a detailed description thereof will be omitted.

Figure 5:
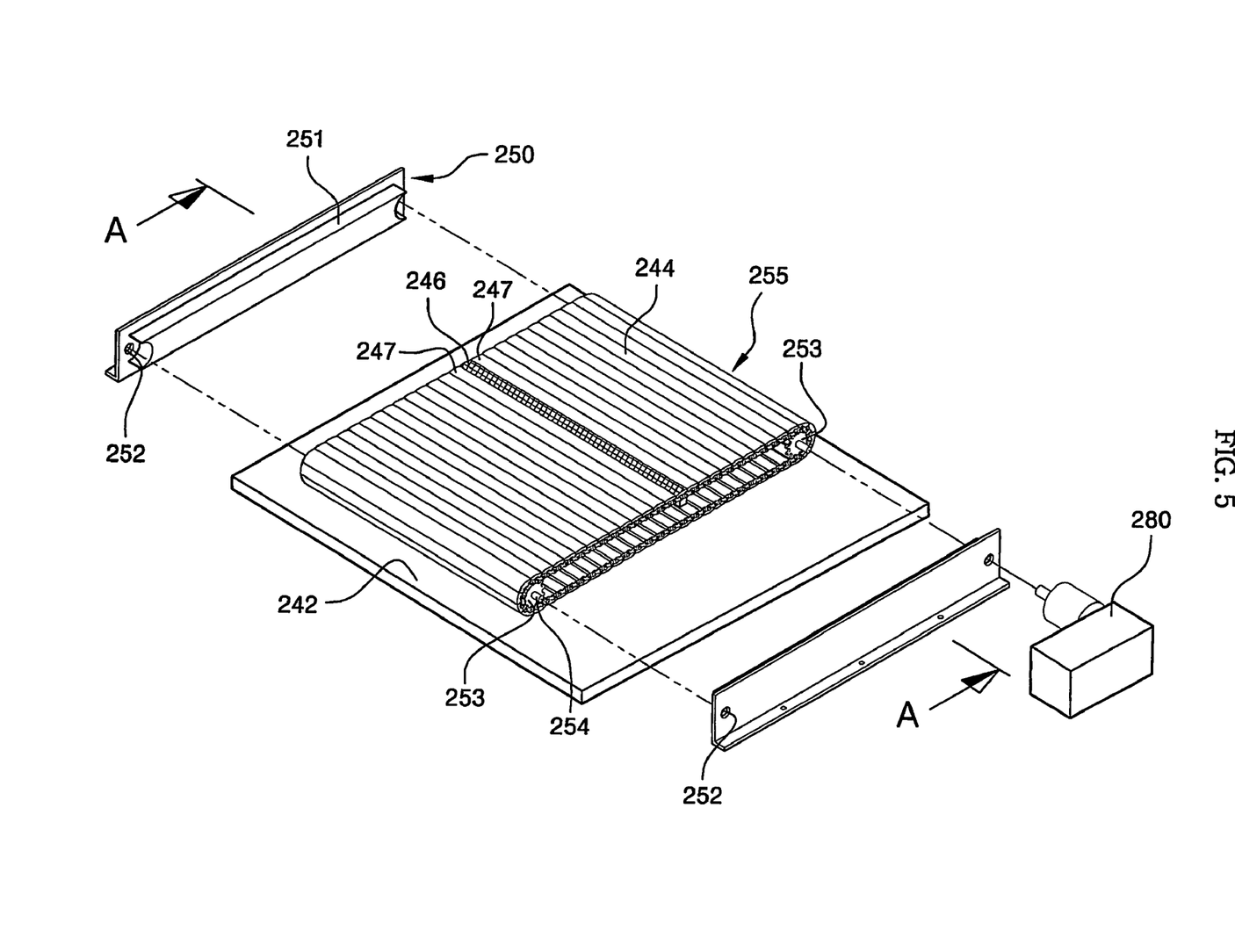
FIG. 5 is a perspective view showing a third embodiment of the scanning unit of the ultrasonic examination apparatus according to the present invention.
Figure 6:
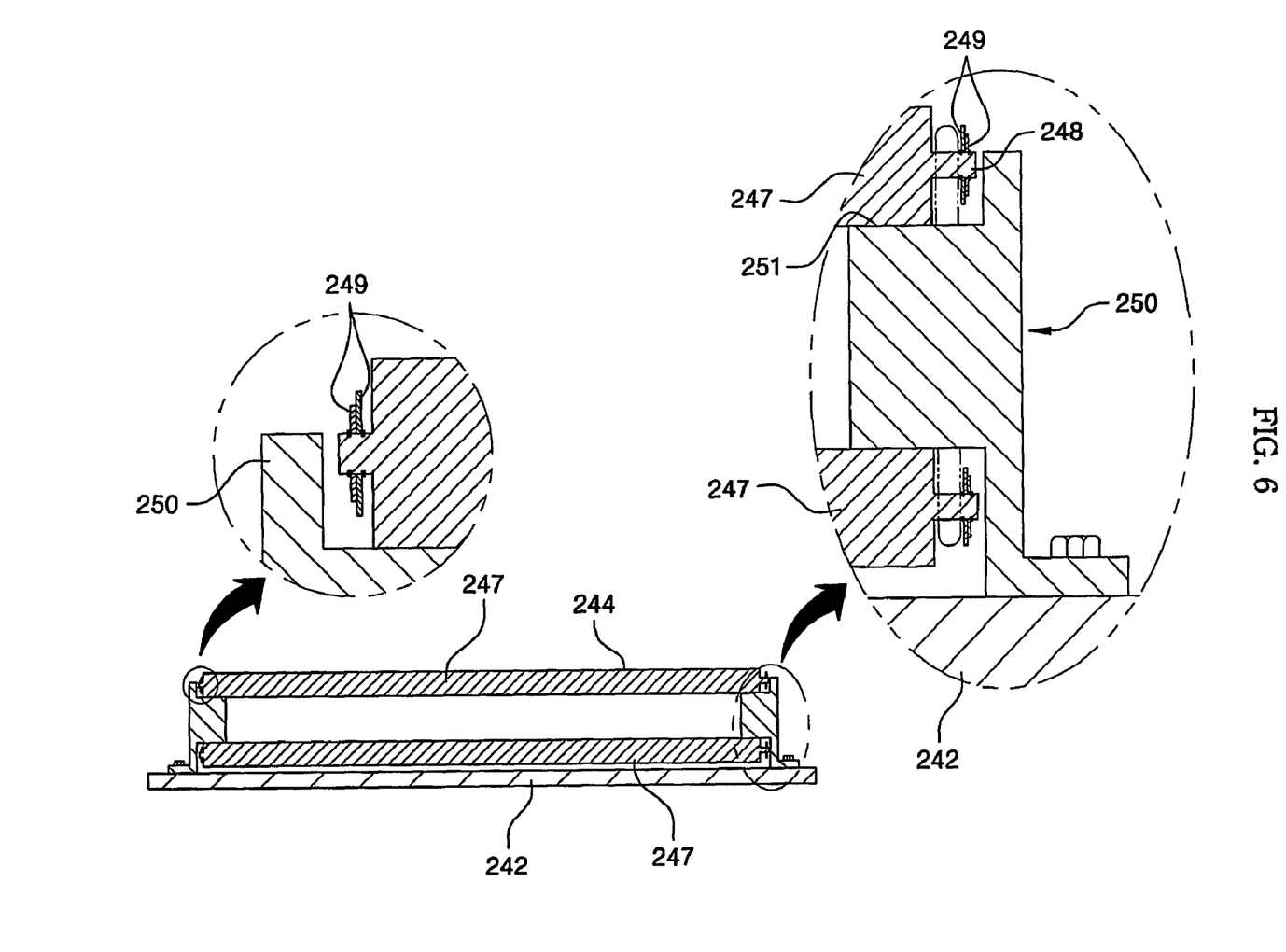
FIG. 6 is a sectional view taken along line A-A in FIG. 5.

FIG. 5 is a view showing a third embodiment of the scanning unit used in the ultrasonic examination apparatus according to the present invention, and FIG. 6 is a sectional view taken along line A-A in FIG. 5.

A scanning unit 240 of this embodiment comprises a caterpillar 255 consisting of a plurality of links 247 each of which has a flat surface 244 on a frame 242, a pair of rollers for internally supporting both longitudinal ends of the caterpillar, and a pair of supporting members 250 for supporting both lateral sides of the caterpillar 255. Further, a driving means 280 is coupled to at least one of the rollers to rotate the caterpillar 255. Particularly, at least one ultrasonic probe 246 is fixedly installed between any two links 247 of the caterpillar 255. Moreover, a pair of sprocket wheels 253 are installed on one side of the caterpillar 255 to move the caterpillar in endless track manner. It is also possible to insert the sprocket wheels 253 at both ends of the caterpillar after eliminating the pair of rollers in order to support the caterpillar 255. A rotational shaft 254 for at least one of the pair of sprocket wheels 253 is connected to a motor shaft of the driving means 280 to move the caterpillar 255 in endless track manner. The supporting members 250 are connected to the frame 242, and the rotational shaft 254 of each of the pair of sprocket wheels 253 extending outward widthwise is inserted into relevant engagement holes 252 of the supporting members 250. Thus, the sprocket wheels 253 are rotatably supported by the supporting members 250.

As shown in FIG. 6, supporting steps 251 of the supporting members 250 are inserted into the caterpillar 255 at the both lateral ends thereof to support the lateral ends of the caterpillar 255. The supporting steps 251 of the supporting members 250 support the both lateral ends of the caterpillar 255, so that even though an object to be examined is placed on the flat surface 244 of the caterpillar 255, the caterpillar 255 can be prevented from sagging due to the weight of the object. That is, since the respective links 247 of the caterpillar 255 have rigidity widthwise of the caterpillar 255 but are connected to one another through chain links 259, the flat surface 244 of the caterpillar 255 sags due to play of the chain links 249 when the breast or the like is placed on the flat surface 244 of the caterpillar 255, if there are no supporting members 250. In this embodiment, however, connections of adjacent two links 247 are supported by the supporting steps 251 of the supporting member 250, thereby preventing the sagging phenomenon. Furthermore, although this embodiment has been described by way of example as having the single ultrasonic probe 246 installed between the two links 247, a plurality of ultrasonic probes 246 may be installed between adjacent links 247, respectively.

Figure 7:
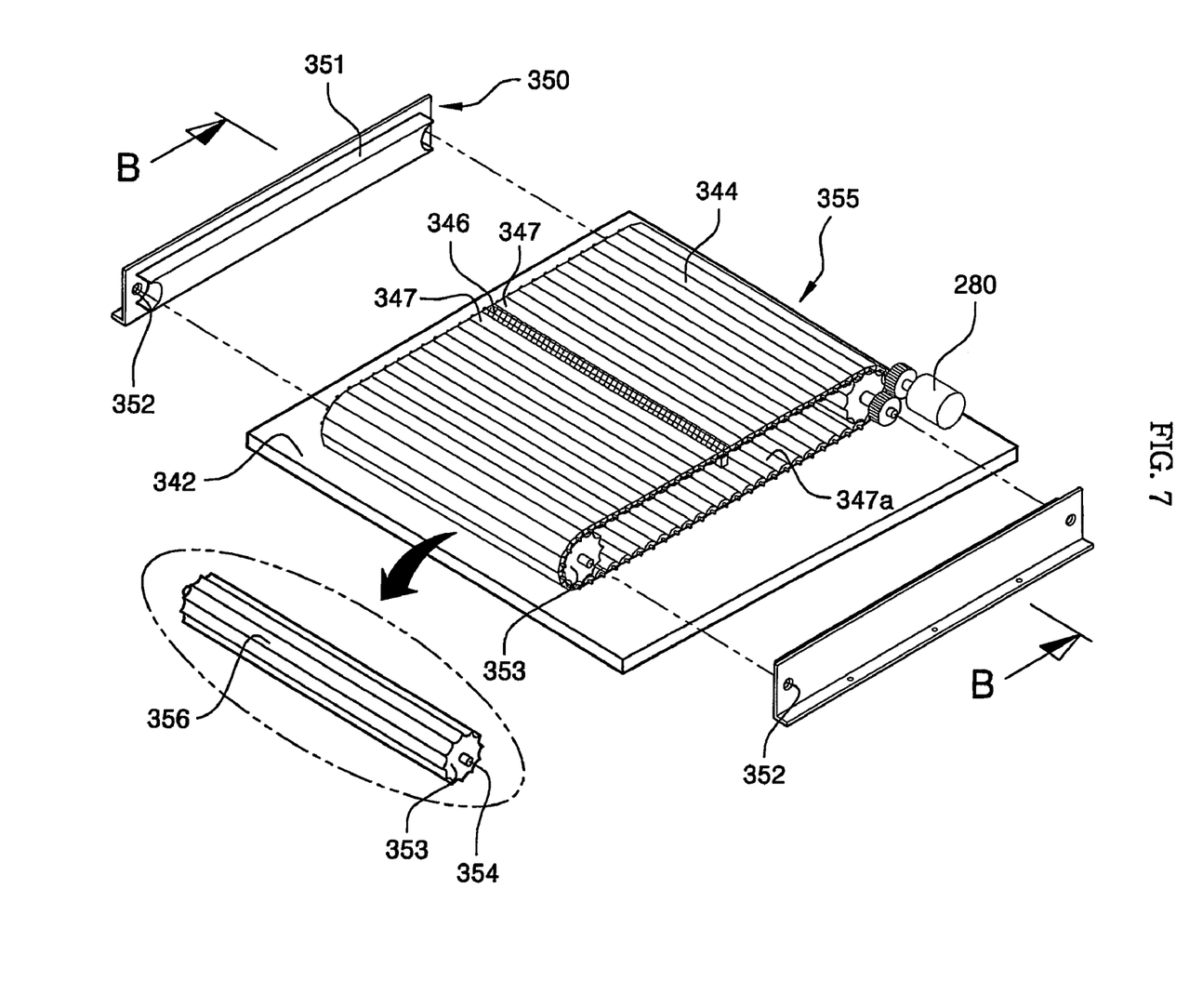
FIG. 7 is a perspective view showing a fourth embodiment of the scanning unit of the ultrasonic examination apparatus according to the present invention.
Figure 8:
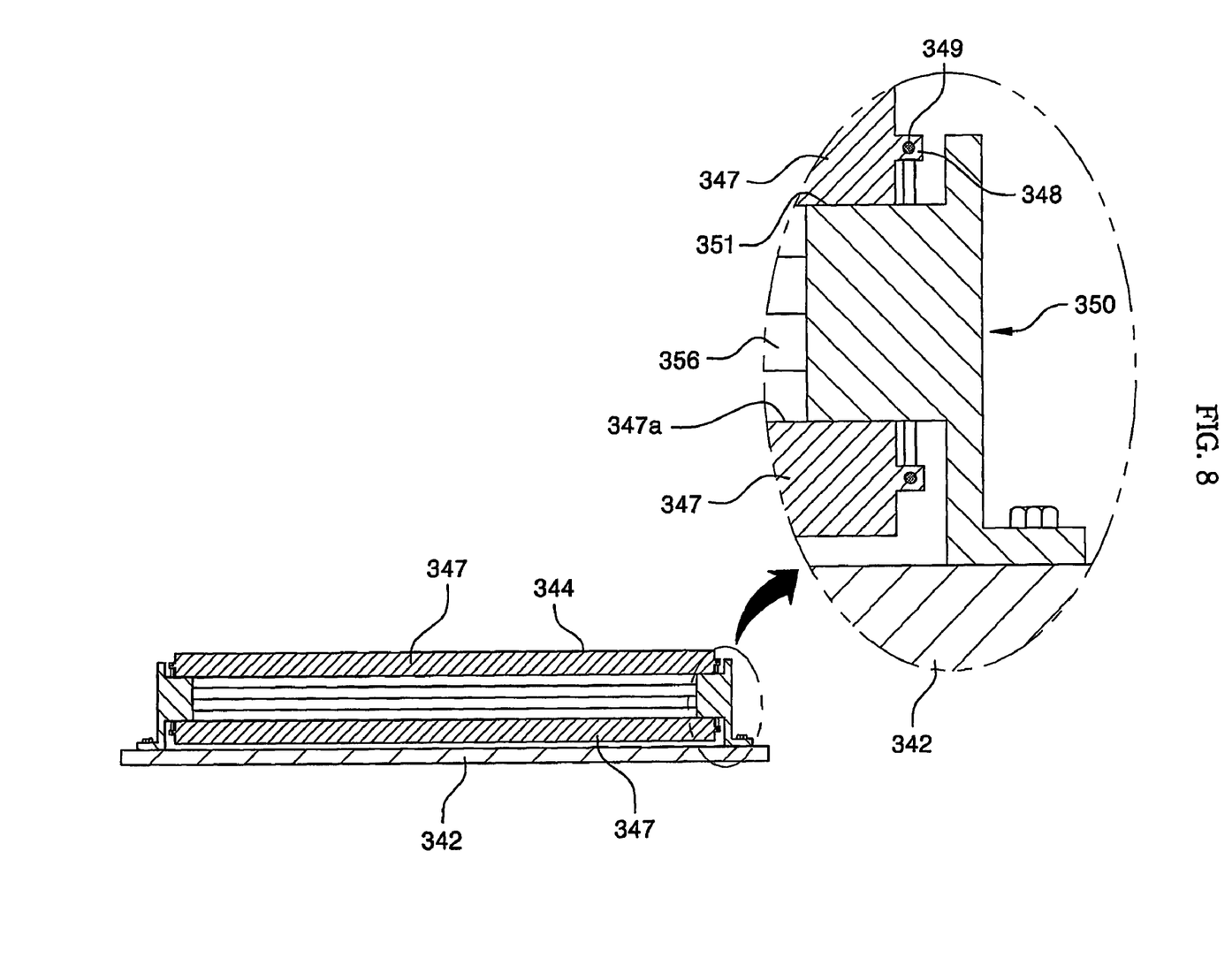
FIG. 8 is a sectional view taken along line B-B in FIG. 7.

FIG. 7 is a view showing a fourth embodiment of the scanning unit used in the ultrasonic examination apparatus according to the present invention, and FIG. 8 is a sectional view taken along line B-B in FIG. 7.

A scanning unit of this embodiment comprises a caterpillar 355 consisting of a plurality of links 347 each of which has a flat surface 344 on a frame 342, a pair of rollers 353 internally supporting both longitudinal ends of the caterpillar 355, and a pair of supporting members 350 for supporting both lateral ends of the caterpillar 355. At least one of the pair of the rollers 353 is interlocked with the caterpillar 355 to move the caterpillar 355 in response to the rotation of the roller. Further, at least one of the rollers 353 is connected to a driving means 380, and at least one ultrasonic probe 346 is fixedly installed between any two links 347 of the caterpillar 355.

As shown in FIG. 7, the interlocking of the roller 353 with the caterpillar 355 is achieved by a plurality receiving grooves 356 longitudinally formed at a regular interval on an outer circumferential surface of the roller 355 and by a plurality of insertion surfaces 347a that have the same cross section in a longitudinal direction and are formed on the back of the flat surface 344 of the links 347 of the caterpillar 355 so that the insertion surfaces can come into close contact with the receiving grooves 356. Accordingly, when the roller 353 connected to the driving means 380 is rotated, the insertion surfaces 347a of the links 347 of the caterpillar 355 are inserted into the receiving grooves 356 of the roller 353, thereby moving the caterpillar 353 in endless track manner.

The supporting members 350 are fixed to the frame 342. A shown in FIG. 8, supporting steps 351 of the respective supporting members 350 are inserted into the caterpillar 355 at the both lateral ends thereof to support the lateral ends of the caterpillar 355. The supporting steps 351 of the supporting members 350 support the both lateral ends of the caterpillar 355, so that even though an object to be examined is placed on the flat surface 344 of the caterpillar 355, the caterpillar 355 can be prevented from sagging due to the weight of the object. Since the respective links 347 of the caterpillar 355 have rigidity widthwise of the caterpillar 355 but are connected to one another through wires 349 at both ends thereof, the flat surface 344 of the caterpillar 355 sags due to the weight of the breast or the like when the breast or the like is placed on the flat surface 344 of the caterpillar 355, if there are no supporting members 350. In the scanning unit of this embodiment, however, connections of adjacent two links 347 are supported by the supporting steps 351 of the supporting member 350, thereby preventing the sagging phenomenon.

INDUSTRIAL APPLICABILITY

According to the ultrasonic examination apparatus of the present invention, a subject can simply go through an examination in a standing posture and a location of a deformable object such as the breast corresponding to ultrasonic examination results can be accurately obtained.

Further, according to the ultrasonic examination apparatus of the present invention, an object to be examined can be automatically scanned from a lower portion thereof without holding an ultrasonic probe with a hand by an inspector and the ultrasonic probe can come into contact with the object to be examined by means of gravity without pressing the object to be examined.

Moreover, according to the ultrasonic examination apparatus of the present invention, an ultrasonic examination can be quickly performed by moving an ultrasonic probe in a state where the location and shape of a deformable object to be examined are maintained, thereby examination with this apparatus can be efficiently performed in case of mass screening of breast cancer.

Further, the ultrasonic examination device of the present invention can adjust freely a height and gradient according to a body type of the subject and can move the ultrasonic probe to examine the overall object to be examined at once.

Furthermore, the ultrasonic examination apparatus of the present invention has advantages in that the height and inclination thereof can be freely adjusted according to the figure of a subject, and the entire object to be examined can be examined only at one time while the ultrasonic probe is moved. Particularly, in the ultrasonic examination apparatus of the present invention, a subject directly places an object to be examined on the gel pad that has been placed on the ultrasonic probe and causes the pressing unit to press the object, thereby eliminating conventional troublesomeness that an inspector causes the object to be examined to be in contact with the ultrasonic probe with his/her hand and then examines the object one by one in order to perform a diagnosis. Therefore, there are advantages in that manpower and time required for the diagnosis can be drastically reduced and the subject can be avoided from discomfort and shame. In addition, since an ultrasonic-examination is performed by moving an elongated ultrasonic probe in the ultrasonic examination of the present invention, a superior image can be obtained even at relatively lower costs.

It is intended that the embodiments of the present invention described above and illustrated in the drawings should not be construed as limiting the technical spirit of the present invention. The scope of the present invention is defined only by the appended claims. Those skilled in the art can make various changes and modifications thereto without departing from its true spirit. Therefore, various changes and modifications obvious to those skilled in the art will fall within the scope of the present invention.

The invention claimed is:

1. A breast scanning device comprising:
an endless loop structure comprising a breast support surface configured to support a substantially entire portion of a breast that is subject to scanning, wherein the breast support surface is configured to move along an endless loop during scanning such that a portion of the breast support surface turns upside down along the endless loop while at the same time the substantially entire portion of the breast is supported by one or more other portions of the breast support surface;
an ultrasonic probe fixed to the endless loop structure and movable along with the breast support surface; and
a compressor comprising a compressor surface opposing the breast support surface and configured to move the compressor surface toward the breast support surface to press the breast that is placed over the breast support surface.

2. The device of claim 1, wherein the ultrasonic probe is movable in a scanning direction of the breast scanning device.

3. The device of claim 2, wherein the ultrasonic probe is elongated and is fixed to the endless loop structure to extend in a direction generally perpendicular to the scanning direction.

4. The device of claim 1, wherein the endless loop comprises a linear portion and two curved portions, each of which is connected at an end of the linear portion.

5. The device of claim 4, wherein the breast support surface comprises a substantially planar portion.

6. The device of claim 5, further comprising a roller configured to rotate and cause to move the endless loop structure.

7. The device of claim 6, further comprising a support configured to support a portion of the endless loop structure so as to make at least part of the breast support surface substantially planar.

8. The device of claim 7, wherein the support is not movable.

9. The device of claim 1, wherein the endless loop structure comprises a belt or a caterpillar track.

10. A method of scanning a breast, the method of comprising:
providing the breast scanning device of claim 1;
placing a breast of a person between the breast support surface and the compressor surface;
moving the endless loop structure along the endless loop, thereby moving the ultrasonic probe in a scanning direction; and
ultrasonically scanning the breast using the ultrasonic probe while moving the ultrasonic probe in the scanning direction.

11. The method of claim 10, wherein the endless loop comprises a linear portion and two curved portions, each of which is connected at an end of the linear portion.

12. The method of claim 10, wherein the scanning direction is substantially parallel to the linear portion.

13. The method of claim 10, wherein a gel pad is located between the breast and the breast support surface.

14. The device of claim 1, wherein consecutive portions of the breast support surface are configured to sequentially support the breast as the breast support surface moves along the endless loop.

* * * * *